(12) United States Patent
Fukae

(10) Patent No.: US 6,784,310 B2
(45) Date of Patent: Aug. 31, 2004

(54) METHODS FOR CRYSTALLIZATION OF N-(1(S)-ETHOXYCARBONYL-3-PHENYLPROPYL)-L-ALANINE N-CARBOXYANHYDRIDE

(75) Inventor: Masafumi Fukae, Hyogo (JP)

(73) Assignee: Kaneka Corporation, Osaka (JP)

( * ) Notice: Subject to any disclaimer, the term of this patent is extended or adjusted under 35 U.S.C. 154(b) by 91 days.

(21) Appl. No.: 10/019,318

(22) PCT Filed: May 15, 2001

(86) PCT No.: PCT/JP01/04059
§ 371 (c)(1),
(2), (4) Date: Apr. 24, 2002

(87) PCT Pub. No.: WO01/87858
PCT Pub. Date: Nov. 22, 2001

(65) Prior Publication Data
US 2002/0137944 A1 Sep. 26, 2002

(51) Int. Cl.⁷ .............................................. C07C 205/00
(52) U.S. Cl. ........................ 560/125; 560/155; 568/215
(58) Field of Search ............................. 560/20, 38, 39, 560/40

(56) References Cited

U.S. PATENT DOCUMENTS

| 4,496,542 A | | 1/1985 | Skiles et al. .................... 514/2 |
| 4,831,184 A | * | 5/1989 | Youssefyeh et al. .......... 560/43 |
| 5,359,086 A | | 10/1994 | Merslavic et al. .......... 548/533 |

FOREIGN PATENT DOCUMENTS

| EP | 0 215 335 | 3/1987 |
| HU | 215 699 B | 3/1999 |
| JP | 2000-270882 | 10/2000 |

* cited by examiner

Primary Examiner—Johann Richter
Assistant Examiner—Karl Puttlitz
(74) Attorney, Agent, or Firm—Westerman, Hattori, Daniels & Adrian, LLP

(57) ABSTRACT

A crystallization is carried out by adding a solution of N-(1(S)-ethoxycarbonyl-3-phenylpropyl)-L-alanine N-carboxylic anhydride in a good solvent to an aliphatic hydrocarbon solvent while inhibiting the oil formation and scaling of said N-carboxylic anhydride.

Further, a crystallization is carried out by adding an aliphatic hydrocarbon solvent sequentially to a solution of N-(1(S)-ethoxycarbonyl-3-phenylpropyl)-L-alanine N-carboxylic anhydride in a good solvent over not less than ¼ of an hour and at a temperature of not higher than 60° C.

51 Claims, No Drawings

METHODS FOR CRYSTALLIZATION OF N-(1(S)-ETHOXYCARBONYL-3-PHENYLPROPYL)-L-ALANINE N-CARBOXYANHYDRIDE

TECHNICAL FIELD

The present invention relates to a crystallization method of N-(1(S)-ethoxycarbonyl-3-phenylpropyl)-L-alanine N-carboxylic anhydride (hereinafter referred to sometimes as compound (1)) represented by the formula (1):

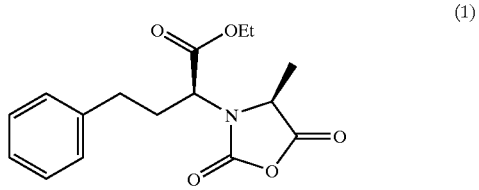

in the formula, all configurations of asymmetric carbon atoms are (S) configurations, which is a common intermediate for a group of compounds which inhibit angiotensin-converting enzyme (ACE) to express a potent antihypertensive action among the therapeutic drugs for hypertension which are on the market today.

BACKGROUND ART

The compound (1) can be obtained by reacting N-(1(S)-ethoxycarbonyl-3-phenylpropyl)-L-alanine (hereinafter referred to sometimes as compound (2)) represented by the formula (2):

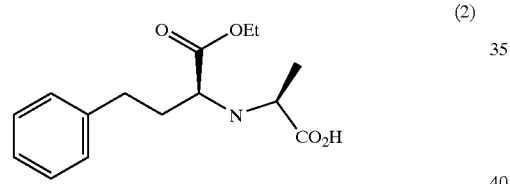

in the formula, all configurations of asymmetric carbon atoms are (S) configurations, with N,N'-carbonyldiimidazole or phosgene. The known mode of use of the above compound (1) includes the mode in which the compound (1) is not isolated from the above-mentioned reaction solution and is directly submitted to the subsequent reaction (JP-A-57-175152, U.S. Pat. No. 5,359,086) and the mode in which the above reaction mixture is distilled under reduced pressure to remove the solvent and concentrated to dryness, the dried solid is crushed, and the resulting white powder is put to use (Reference Example in JP-B-05-41159).

These conventional modes of use of the compound (1) have several drawbacks for commercial exploitation. For example, in the mode of use in which the reaction solution is directly submitted to the subsequent reaction, the reaction solvent species which can be used in the subsequent reaction is limited, unless a solvent exchange procedure is interposed, to the solvent species used in the N-carboxylic anhydride-forming reaction (hereinafter referred to as NCA forming reaction) or to a mixed solvent containing the solvent used in the NCA forming reaction. Furthermore, since the transfer and storage in a form of a solution is required, this mode of use has the disadvantage of inconvenience in the handling of this versatile intermediate compound.

Further, it is known from JP-B-05-41159 that compound (1) can be obtained in a powdery form but because the powder is acquired by concentrating to dryness the solution following the NCA forming reaction, the concomitant impurity is not removed and this procedure is not easy to follow on a commercial scale.

While the inventors of the present invention studied on the course of crystallization of the compound (1), it was found that in the crystallization of the compound (1) on a commercial scale, an oil formation and scaling tend to occur with high frequency so that it is difficult to effect stable crystallization on a commercial scale. It was also found difficult to obtain crystals of high purity and good powder characteristics.

SUMMARY OF THE INVENTION

As the result of an intensive investigation for overcoming the above disadvantages, the inventors of the present invention discovered a crystallization method by which crystals of the compound (1) can be obtained in a stable manner with good workability avoiding an oil formation and scaling and with a large mean crystal particle diameter and good powder characteristics and which can be carried into practice on a commercial scale, and have ultimately developed the present invention.

The first aspect of the present invention, therefore, is concerned with a crystallization method of N-(1(S)-ethoxycarbonyl-3-phenylpropyl)-L-alanine N-carboxylic anhydride which comprises mixing a solution of N-(1(S)-ethoxycarbonyl-3-phenylpropyl)-L-alanine N-carboxylic anhydride in a good solvent with an aliphatic hydrocarbon solvent to crystallize said N-carboxylic anhydride, the solution of said N-carboxylic anhydride in the good solvent being added to the aliphatic hydrocarbon solvent to thereby effect crystallization, while inhibiting an oil formation and scaling of said N-carboxylic anhydride.

The second aspect of the present invention, therefore, is concerned with a crystallization method of N-(1(S)-ethoxycarbonyl-3-phenylpropyl)-L-alanine N-carboxylic anhydride which comprises adding an aliphatic hydrocarbon solvent to a solution of N-(1(S)-ethoxycarbonyl-3-phenylpropyl)-L-alanine N-carboxylic anhydride in a good solvent to crystallize said N-carboxilic anhydride, the aliphatic hydrocarbon solvent being added sequentially over not less than ¼ of an hour and at a temperature of not higher than 60° C. to thereby inhibit an oil formation and scaling of said N-carboxylic anhydride.

The present invention is now described in detail.

DISCLOSURE OF INVENTION

The first aspect of the invention is now described.

In this invention, a solution of said compound (1) in a good solvent is mixed with an aliphatic hydrocarbon solvent to crystallize the compound (1). In order to carry out the crystallization of the compound (1) with advantage, the presence of the aliphatic hydrocarbon solvent is essential.

The aliphatic hydrocarbon solvent mentioned above is not particularly restricted but includes, for example, chain saturated hydrocarbons of 5 to 12 carbon atoms represented by $C_nH_{2n+2}$, such as pentane, 2-methylpentane, 2,2-dimethylpentane, normal hexane, isohexane, normal heptane, normal octane, isooctane, normal decane, etc.; cyclic saturated hydrocarbons of 5 to 12 carbon atoms represented by $C_nH_{2n}$, such as methylcyclopentane, ethylcyclopentane, propylcyclopentane, cyclohexane, methylcyclohexane, ethylcyclohexane, propylcyclohexane, etc.; and mixed solvents thereof. Furthermore, unsaturated hydrocarbons of 5 to 12 carbon atoms represented by $C_nH_{2n}$ or $C_nH_{2n-2}$, such as 2-pentene, 1-hexane, cyclohexene, etc. and mixed solvents thereof or their mixed solvents with said saturated hydrocarbons can also be used.

Among these, chain or cyclic saturated hydrocarbons of 5 to 12 carbon atoms represented by $C_nH_{2n+2}$ or $C_nH_{2n}$ and mixed solvents thereof are suitable. Not only from crystallization points of view but also in consideration of drying time of obtained crystals, the industrially preferred aliphatic hydrocarbon solvent includes saturated hydrocarbons of 5 to 10 carbon atoms represented by $C_nH_{2n+2}$ or $C_nH_{2n}$ and mixed solvents thereof.

Preferred among these are pentane, 2-methylpentane, 2,2-dimethylpentane, normal hexane, isohexane, normal heptane, normal octane, isooctane, methylcyclopentane, cyclohexane, methylcyclohexane, ethylcyclohexane, propylcyclohexane, and mixed solvents thereof. Further, more preferred are pentane, 2-methylpentane, normal hexane, isohexane, normal heptane, normal octane, cyclohexane, methylcyclohexane, ethylcyclohexane, propylcyclohexane, and mixed solvents thereof. Particularly, normal hexane, isohexane, normal heptane, methylcyclohexane, and mixed solvents thereof are suitable, and normal hexane, normal heptane and a mixed solvent thereof are still more suitable.

The good solvent mentioned above is not particularly restricted but includes, for example, halogenated hydrocarbons such as dichloromethane, 1,1-dichloroethane, 1,2-dichloroethane, 1,1,1-trichloroethane, 1,1,2-trichloroethane, etc.; ethers such as tetrahydrofuran, 1,4-dioxane, t-butyl methyl ether, etc.; nitriles such as acetonitrile, etc.; esters such as ethyl acetate, methyl acetate, propyl acetate, isopropyl acetate, butyl acetate, isobutyl acetate, pentyl acetate, methyl propionate, ethyl propionate, etc.; ketones such as acetone, methyl ethyl ketone, etc.; aromatic hydrocarbons such as toluene etc.; and mixed solvents thereof. More particularly, dichloromethane, 1,2-dichloroethane, tetrahydrofuran, 1,4-dioxane, acetonitrile, ethyl acetate, methyl acetate, isopropyl acetate, acetone, methyl ethyl ketone and toluene are preferred.

Among these, said halogenated hydrocarbons, ethers, and esters are suitable, and halogenated hydrocarbons are particularly suitable. The preferred halogenated hydrocarbons are dichloromethane, 1,1-dichloroethane, 1,2-dichloroethane, 1,1,1-trichloroethane, 1,1,2-trichloroethane and mixed solvents thereof, and dichloromethane and 1,2-dichloroethane are preferred among these. Particularly preferred is dichloromethane. Needless to say, other solvents may be contained within the range not causing adverse effects.

In the first aspect of the present invention, mixing of the solution of said compound (1) in the good solvent with the aliphatic hydrocarbon solvent is carried out by the method comprising adding the solution of said compound (1) in the good solvent to the aliphatic hydrocarbon solvent.

The temperature at addition of the solution in the good solvent is preferably not higher than 60° C. but in order to manifest the effect of the invention to the maximum extent, the temperature at addition of the solution in the good solvent is more preferably −30 to 50° C., still more preferably −20 to 45° C.

The addition of the solution of said compound (1) in the good solvent to the aliphatic hydrocarbon solvent is preferably carried out by a sequential addition of the solution in the good solvent. Such sequential addition is preferably carried out over not less than ¼ of an hour and for better crystallization, more preferably over not less than ½ of an hour, still more preferably over not less than an hour.

In the crystallization according to the first aspect of the present invention, much better crystallization in which the oil formation and scaling will not substantially occur can be carried out by adding the solution of the compound (1) in the good solvent in such condition that a certain amount of crystals of the compound (1) is added in the aliphatic hydrocarbon solvent in advance. Specifically, crystallization is carried out by adding crystals of said compound (1) to the aliphatic hydrocarbon solvent at the level of preferably not more than 30 weight %, more preferably not more than 20 weight %, still more preferably not more than 5 weight % (the lower limit is usually 0.1 weight %) based on the total amount of said compound (1) in the solution in the good solvent to be added to thereby prepare a crystal slurry of said compound (1), and adding, preferably sequentially, the solution of the compound (1) in the good solvent to the above slurry.

The same effect can be achieved by adding a portion of the solution of the compound (1) in the good solvent to the aliphatic hydrocarbon solvent in advance to prepare a slurry in which said compound (1) is precipitated followed by adding the rest of the solution in the good solvent to the above slurry. Specifically, crystallization in which the oil formation and scaling will not substantially occur can be carried out by adding, preferably sequentially, the solution in the good solvent preferably not more than 30 weight %, more preferably not more than 20 weight %, still more preferably not more than 10 weight % (the lower limit is usually 0.5 weight %) based on the total amount of the solution of said compound (1) in the good solvent to be added to the aliphatic hydrocarbon solvent in advance, to thereby prepare a crystal slurry of said compound (1) and adding, preferably sequentially, the rest of the solution in the good solvent. In the case where a portion of the solution of said compound (1) in the good solvent is added to the aliphatic hydrocarbon solvent to prepare a crystal slurry in advance, the addition of the solution of said compound (1) in the good solvent is carried out, for example, over not less than ⅒ of an hour, but for better precipitation of crystals, the addition is carried out preferably over not less than ⅕ of an hour, more preferably over not less than ½ of an hour.

Needless to say, gradual addition of the whole amount of the solution of the compound (1) in the good solvent to the aliphatic hydrocarbon solvent continuously or separately over a protracted time period is equivalent to continuously carrying out the above procedure of preparing a crystal slurry of the above compound (1) in advance, followed by adding the solution in the good solvent, so that a similar inhibition effect of the oil formation and scaling can be expected.

The retention time following addition of the solution of said compound (1) in the good solvent to the aliphatic hydrocarbon solvent is not particularly restricted but is usually not less than about ½ of an hour.

The ratio of the good solvent to the aliphatic hydrocarbon solvent at completion of addition varies according to the combination of the good solvent and aliphatic hydrocarbon solvent to be used and the concentration of the compound (1) in the solution in the good solvent to be used, but in consideration of productivity and the like, is preferably 0.001 to 1, more preferably 0.003 to 1, still more preferably 0.003 to 0.8, particularly preferably 0.01 to 0.5, as the weight ratio of the good solvent to the aliphatic hydrocarbon solvent.

Specifically, when a halogenated hydrocarbon is used as the good solvent, the ratio is preferably 0.003 to 1, more preferably 0.01 to 0.5. When an aprotic polar solvent such as tetrahydrofuran, acetonitrile or acetone is used as the good solvent, the ratio is preferably 0.01 to 0.7, more preferably 0.05 to 0.5. When an ester such as ethyl acetate, or an aromatic hydrocarbon such as toluene is used as the good solvent, the ratio is preferably 0.06 to 0.8, more preferably 0.1 to 0.5.

In the above crystallization procedure, by adjusting the ratio of the good solvent to the aliphatic hydrocarbon solvent ultimately to a predetermined ratio, not less than 80 weight %, preferably not less than 90 weight %, more preferably not less than 95 weight % of the total amount of said compound (1) can be precipitated with inhibiting oil formation and with the amount of scaling being inhibited to not more than 10 weight %, preferably not more than 8 weight % of the total amount, thus enabling production of crystals of said compound (1) with a high recovery rate.

In the first aspect of the invention, it is preferred to increase the amount of precipitated crystals by adjusting the liquid temperature to not higher than 25° C. after completion of addition of the solution in the good solvent to the aliphatic hydrocarbon solvent and before isolating crystals precipitated. The above liquid temperature is more preferably −30 to 25° C., still more preferably −20 to 15° C. In this manner, crystals can be caused to precipitate sufficiently and be obtained with a high recovery rate.

The crystallization method of the invention can be used not only as the recrystallization method of the compound (1) but also as the method of isolating the compound (1) from the reaction solution.

The solution of the compound (1) in the good solvent for use in this invention may optionally be an NCA forming reaction solution obtained by reacting said compound (2) with N,N'-carbonyldiimidazole or phosgene (inclusive of dimeric and trimeric phosgenes) in said good solvent. The solvent for such an NCA forming reaction is not particularly restricted inasmuch as it is stable in the NCA forming reaction. Thus, for example, the above-mentioned halogenated hydrocarbons, ethers, esters, nitriles, ketones and mixed solvents thereof can be preferably used. Specifically, halogenated hydrocarbons such as dichloromethane and 1,2-dichloroethane, etc.; ethers such as tetrahydrofuran and 1,4-dioxane, etc.; esters such as ethyl acetate, etc.; nitriles such as acetonitrile, etc.; and ketones such as acetone and methyl ethyl ketone, etc., can be generally and suitably used. Preferred among these are halogenated hydrocarbons and dichloromethane is particularly preferred.

The solvent species to be used for crystallization is not necessarily identical with the solvent species used for said NCA forming reaction. Thus, the solution of compound (1) in the good solvent for use in this invention may be the solution, after the NCA forming reaction, subjected to one or a several cycles of concentration for removing the low-boiling-point component including the reaction solvent (inclusive of phosgene and hydrogen chloride gas when phosgene is used) or the solution obtained by exchanging the reaction solvent with a solvent suitable for crystallization. Needless to say, it is convenient that the reaction solvent doubles as the crystallization solvent (good solvent). For example, when a halogenated hydrocarbon such as dichloromethane is used as the NCA forming reaction solvent and phosgene is used as the NCA forming reagent, the reaction mixture at completion of the reaction can be concentrated to adjust the concentration of the compound (1) and this can preferably be used as the solution of the compound (1) in the good solvent.

In order to obtain high-quality crystals of the compound (1), it is preferable to remove an impurity and a coloring component as the by product of said NCA forming reaction by using an adsorbent (preferably activated carbon) prior to the crystallization of the present invention.

The crystals thus obtained can be separated by the ordinary solid-liquid separation processes, such as centrifugation, pressure filtration or suction filtration, preferably washed with an aliphatic hydrocarbon solvent, and optionally dried by atmospheric pressure drying or reduced pressure drying (vacuum drying).

In accordance with this first aspect of the present invention, the crystallization can be carried out in a satisfactory manner while the oil formation and scaling of said compound (1) are inhibited so that crystals of compound (1) can be obtained with a high recovery rate.

The second aspect of the present invention is now described.

In the second aspect of the present invention, an aliphatic hydrocarbon solvent is added to a solution of said compound (1) in a good solvent to crystallize the compound (1). To carry out the crystallization of the compound (1) with advantage, the presence of an aliphatic hydrocarbon solvent is essential.

The aliphatic hydrocarbon solvent mentioned above is not particularly restricted but includes, for example, chain saturated hydrocarbons of 5 to 12 carbon atoms represented by $C_nH_{2n+2}$, such as pentane, 2-methylpentane, 2,2-dimethylpentane, normal hexane, isohexane, normal heptane, normal octane, isooctane, normal decane, etc.; cyclic saturated hydrocarbons of 5 to 12 carbon atoms represented by $C_nH_{2n}$, such as cyclopentane, methylcyclopentane, ethylcyclopentane, propylcyclopentane, cyclohexane, methylcyclohexane, ethylcyclohexane, propylcyclohexane, etc.; and mixed solvents thereof. Furthermore, unsaturated hydrocarbons of 5 to 12 carbon atoms represented by $C_nH_{2n}$ or $C_nH_{2n-2}$, such as 2-pentene, 1-hexene, cyclohexene, etc. and mixed solvents thereof or their mixed solvents with said saturated hydrocarbons can also be used.

Among these, chain or cyclic saturated hydrocarbons of 5 to 12 carbon atoms represented by $C_nH_{2n+2}$ or $C_nH_{2n}$ and mixed solvents thereof are suitable. Not only from crystallization points of view but also in consideration of drying time of obtained crystals, the industrially more preferred aliphatic hydrocarbon solvent includes chain or cyclic saturated hydrocarbons of 5 to 10 carbon atoms represented by $C_nH_{2n+2}$ or $C_nH_{2n}$ and mixed solvents thereof.

Among these, pentane, 2-methylpentane, 2,2-dimethylpentane, normal hexane, isohexane, normal heptane, normal octane, isooctane, normal decane, cyclopentane, methylcyclopentane, cyclohexane, methylcyclohexane, ethylcyclohexane, propylcyclohexane, and mixed solvents thereof are preferred. In particular, normal hexane, isohexane, normal heptane, isooctane, methylcyclohexane and mixed solvents thereof are suitable. Still more suitable are normal hexane, normal heptane and a mixed solvent thereof.

The good solvent mentioned above is not particularly restricted but includes, for example, halogenated hydrocarbons such as dichloromethane, 1,1-dichloroethane, 1,2-dichloroethane, 1,1,1-trichloroethane, 1,1,2-trichloroethane, etc.; ethers such as tetrahydrofuran, 1,4-dioxane, t-butyl methyl ether, etc.; nitriles such as acetonitrile etc.; esters such as ethyl acetate, methyl acetate, propyl acetate, isopropyl acetate, butyl acetate, isobutyl acetate, pentyl acetate, methyl propionate, ethyl propionate, etc.; ketones such as acetone, methyl ethyl ketone, etc.; aromatic hydrocarbons such as toluene etc.; and mixed solvents thereof. Specifically, dichloromethane, 1,2-dichloroethane, tetrahydrofuran, 1,4-dioxane, acetonitrile, ethyl acetate, methyl acetate, isopropyl acetate, acetone and methyl ethyl ketone are preferred.

Among these, the above-mentioned halogenated hydrocarbons, ethers, and esters are suitable, and halogenated hydrocarbons are particularly suitable. As halogenated hydrocarbons, dichloromethane, 1,1-dichloroethane, 1,2-dichloroethane, 1,1,1-trichloroethane, 1,1,2-trichloroethane and mixed solvents thereof are preferred and among these, dichloromethane and 1,2-dichloroethane are preferred. Particularly preferred is dichloromethane. Needless to say, other solvents maybe contained within the range not causing adverse effects.

The conditions at the time of addition of the aliphatic hydrocarbon solvent are now described.

The addition of the aliphatic hydrocarbon solvent to the solution of said compound (1) in the good solvent is carried out by the sequential addition. The sequential addition may be carried out by adding said solution in the good solvent continuously or separating said solution in the good solvent into several portions and adding them serially.

The time period over which said sequential addition is carried out depends on the temperature, concentration and degree of stirring at the time of addition but generally the addition of the whole amount of the predetermined aliphatic hydrocarbon solvent is carried out over not less than ¼ of an hour. In order to obtain crystals with large particle diameter, the sequential addition is carried out preferably over not less than ½ of an hour, more preferably not less than an hour.

The temperature at which the aliphatic hydrocarbon solvent is added is not higher than 60° C. in order to inhibit the oil formation and scaling. In order to manifest the effect of the invention to the maximum extent, −30 to 50° C. is more preferred, and 0 to 45° C. is still more preferred in order to stably obtain crystals with large particle diameter. The retention time following addition of the aliphatic hydrocarbon solvent is not particularly restricted but generally a period of time not less than about ½ of an hour is sufficient.

In accordance with the second aspect of the present invention, it is preferable to provide sufficient stirring during addition of the aliphatic hydrocarbon solvent in order to inhibit the oil formation and scaling. The intensity of stirring being expressed in a stirring power required per unit volume, it is generally preferable to carry out the addition under stirring with a stirring force of not less than 0.1 kW/m$^3$, more preferably a stirring force of not less than 0.3 kW/m$^3$, being expressed in the stirring power required per unit volume.

As the addition in accordance with the crystallization method of the second aspect of the present invention, it is more advantageous to prepare a slurry of N-carboxylic anhydride in advance (preliminary crystallization) and add the aliphatic hydrocarbon solvent sequentially to said slurry, in which case the oil formation and scaling can be consistently inhibited and, at the same time, crystals with large particle diameter can be obtained.

The suspension amount of the slurry to be prepared in advance in the above preliminary crystallization is not particularly restricted but in consideration of productivity and the like, it is preferably not more than 30 weight %, more preferably not more than 20 weight %, still more preferably not more than 10 weight %, based on the total amount of said N-carboxylic anhydride at completion of crystallization. The lower limit is usually 0.1 weight %.

The slurry in preliminary crystallization may be formed by adding a predetermined amount of the aliphatic hydrocarbon solvent sequentially to the solution of said N-carboxylic anhydride in the good solvent (preliminary crystallization) so as to adjust a mixing composition of the good solvent and the aliphatic hydrocarbon solvent to the composition in which a portion of the compound (1) crystallizes for nucleation or by adding crystals of said N-carboxylic anhydride to the solution of said N-carboxylic anhydride in the good solvent. It is also possible to use both techniques together.

The preferred mixing composition to achieve said suspension amount cannot be defined based on crystallization concentrations and solvent species to be used but, when the aliphatic hydrocarbon solvent is added to the solution of the compound (1) in the good solvent, the weight ratio of the good solvent to the aliphatic hydrocarbon solvent is preferably 0.1 to 10, more preferably 0.1 to 5, still more preferably 0.1 to 3.

As specific examples, when dichloromethane, tetrahydrofuran, acetonitrile or acetone is used as the good solvent, the weight ratio of the good solvent to the aliphatic hydrocarbon solvent for attaining the suspension amount of the slurry in said preliminary crystallization is preferably 0.2 to 5, more preferably 0.2 to 3, and when ethyl acetate, toluene or the like is used as the good solvent, the weight ratio of the good solvent to the aliphatic hydrocarbon solvent for attaining the above suspension amount is preferably 0.3 to 7, more preferably 0.3 to 5. For carrying out satisfactory nucleation and crystal growth in the preliminary crystallization, the aliphatic hydrocarbon solvent is preferably added in portions or continuously so that crystals will not precipitate all at once in the preliminary crystallization. Thus, the time period of addition is not less than ⅕ of an hour, and for satisfactory nucleation and crystal growth, generally about ½ of an hour, more preferably it is required not less than ½ of an hour.

In cases where a preliminary crystallization slurry is prepared by adding crystals of the above N-carboxylic anhydride to the solution of said N-carboxylic anhydride in the good solvent, it is advantageous to control the concentration of the solution of said N-carboxylic anhydride in the good solvent not more than the vicinity of the solubility saturation point. It can be carried out by adjusting the concentration of the solution of the above N-carboxylic anhydride in the good solvent or the temperature of the solution and/or by adding the aliphatic hydrocarbon solvent in a predetermined amount.

Needless to say, the procedure of carrying out the sequential addition of the aliphatic hydrocarbon solvent to the solution of said N-carboxylic anhydride in the good solvent over a protracted time and the procedure of stopping the addition of the aliphatic hydrocarbon solvent at the time when precipitation of crystals begins to allow the crystals to grow or otherwise controlling the precipitation rate of crystals followed by adding a rest of predetermined amount of the aliphatic hydrocarbon solvent can be expected to bring about the same effect as the crystallization involving said preliminary crystallization.

Now, the relationship of addition levels of the good solvent and the aliphatic hydrocarbon solvent in the crystallization according to the second aspect of the present invention is now described.

At completion of addition of the aliphatic hydrocarbon solvent, the ratio of the good solvent to the aliphatic hydrocarbon solvent varies according to the combination of the good solvent and the aliphatic hydrocarbon solvent to be used and the concentration of the compound (1) in the solution in the good solvent to be used but in consideration of productivity and other factors, the weight ratio of the good solvent to the aliphatic hydrocarbon solvent is preferably 0.001 to 1, more preferably 0.003 to 0.8, still more preferably 0.01 to 0.5.

Specifically, when a halogenated hydrocarbon is used as the good solvent, the ratio is preferably 0.003 to 1, more preferably 0.01 to 0.5. When an aprotic polar solvent such as tetrahydrofuran, acetonitrile or acetone is used as the good solvent, the ratio is preferably 0.01 to 0.7, more preferably 0.05 to 0.5, and when an ester such as ethyl acetate, or an aromatic hydrocarbon such as toluene is used as the good solvent, the ratio is preferably 0.06 to 0.8, more preferably 0.1 to 0.5.

In the above crystallization, by adjusting the ratio of the good solvent to the aliphatic hydrocarbon solvent ultimately to a predetermined ratio, not less than 80 weight %, more preferably not less than 90 weight %, still more preferably not less than 95 weight %, of the total amount of said compound (1) can be precipitated and crystals of the above compound (1) not smaller than 200 $\mu$m in mean crystal particle diameter can be obtained with a high recovery rate with inhibiting oil formation and with inhibiting scaling amount to not more than 5 weight %, preferably not more than 3 weight %, of the total amount.

In the second aspect of the present invention, it is preferred to increase the amount of precipitated crystals by adjusting the liquid temperature to not higher than 25° C. after completion of addition of the aliphatic hydrocarbon solvent to the solution in the good solvent and before isolating crystals precipitated. The above liquid temperature is more preferably −30 to 25° C., still more preferably −20 to 15° C. In this manner, crystals can be caused to precipitate sufficiently and be obtained with a high recovery rate.

The crystallization method of this invention can be used not only as the recrystallization method of the compound (1) but also as the method of isolating the compound (1) from the reaction solution.

The solution of said compound (1) in the good solvent is the same as described hereinbefore.

The crystals thus obtained can be separated by the ordinary solid-liquid separation processes such as centrifugation, pressure filtration and suction filtration, preferably washed with an aliphatic hydrocarbon solvent, and optionally dried by atmospheric pressure drying or reduced pressure drying (vacuum drying).

In accordance with the second aspect of the present invention, the crystallization can be carried out with good workability while the oil formation and scaling of the above compound (1) are inhibited so that crystals of the compound (1) not smaller than generally about 200 $\mu$m in mean particle diameter and having good powder characteristics can be obtained stably with a high recovery rate. Obtaining the compound (1) stably as crystals with large particle diameter is expected to contribute a great deal to the stabilization of the unstable compound (1) during long-term storage or the storage at high temperature.

BEST MODE FOR CARRYING OUT THE INVENTION

The following Examples and Reference Production Example illustrate the present invention in further detail without restricting the scope of the invention in any manner.

In Examples and Reference Production Example given hereunder, the assay of N-(1(S)-ethoxycarbonyl-3-phenylpropyl)-L-alanine N-carboxylic anhydride was carried out by derivatizing said N-carboxylic anhydride in the form of a solution or crystals into the corresponding ethyl ester in triethylamine-containing ethanol followed by HPLC analysis as follows.

Analytical Conditions

Chromatograph: Shimadzu Corporation's LC-9A
Column: Nippon Bunko Co.'s ODS column, Finepak SIL-C18-5, 4.6 mm×250 mm
Eluent: acetonitrile/60 mM phosphate buffer=35/65 (v/v)
Flow rate: 0.8 ml/min.
Detection: 210 nm (UV detector)
Temperature: 30° C.

Preparation Example of a Solution in a Good Solvent

Preparation of a Solution of N-(1(S)-ethoxycarbonyl-3-phenylpropyl)-L-alanine N-carboxylic Anhydride in a Good Solvent A 2 L four-necked round-bottom flask equipped with a reflux condenser was charged with 25 g (89.6 mmol) of N-(1(S)-ethoxycarbonyl-3-phenylpropyl)-L-alanine and 500 ml of dichloromethane, and 32 g of phosgene was bubbled with stirring. Then, the mixture was refluxed with heating on an oil bath at 50° C. for 8 hours. After the reaction, dichloromethane (containing phosgene and hydrogen chloride gas) was distilled off under reduced pressure. To the residue was added dichloromethane to give a solution of about 62 weight % of N-(1(S)-ethoxycarbonyl-3-phenylpropyl)-L-alanine N-carboxylic anhydride concentration (yield 98%).

EXAMPLE 1

A solution of N-(1(S)-ethoxycarbonyl-3-phenylpropyl)-L-alanine N-carboxylic anhydride in dichloromethane as prepared by the procedure according to the preparation example of a solution in a good solvent, 63.2 g (62 wt. % concentration), was added to 250 ml of normal hexane over 1 hour at −12° C. and the mixture was stirred at the same temperature for 1 hour (the weight ratio of good solvent/aliphatic hydrocarbon solvent was 0.15). The precipitated crystals of N-(1(S)-ethoxycarbonyl-3-phenylpropyl)-L-alanine N-carboxylic anhydride were collected by suction filtration using a Buchner funnel and washed with 50 ml of normal hexane. After filtration, the scale adherent on the vessel wall was separately dried and its amount was confirmed to be about 6 weight % of the total amount. Substantially no oil formation occurred. The wet cells obtained were dried under vacuum at 25° C. for 15 hours to give 37.2 g of a dry product (recovery rate 93%, chemical purity 98%, optical purity not less than 99% e.e., mean particle diameter 50 $\mu$m).

EXAMPLE 2

A solution of N-(1(S)-ethoxycarbonyl-3-phenylpropyl)-L-alanine N-carboxylic anhydride in dichloromethane as prepared by the procedure according to the preparation example of a solution in a good solvent, 63.2 g (62 wt. % concentration), was added to 250 ml of normal hexane over 30 minutes at 45° C. and the mixture was stirred at the same temperature for 30 minutes. Then, the mixture was further cooled to 5° C. over 4 hours and stirred at the same temperature for 1 hour (the weight ratio of good solvent/aliphatic hydrocarbon solvent was 0.15). The precipitated crystals of N-(1(S)-ethoxycarbonyl-3-phenylpropyl)-L-alanine N-carboxylic anhydride were collected by suction filtration using a Buchner funnel and washed with 100 ml of normal hexane. After filtration, the scale adherent on the vessel wall was separately dried and its amount was confirmed to be about 8 weight % of the total amount. Substantially no oil formation occurred. The wet crystals obtained were dried under vacuum at 25° C. for 15 hours to give 36.8 g of a dry product (recovery rate 92%, chemical purity 98%, optical purity not less than 99% e.e., mean particle diameter 20 μm).

EXAMPLE 3

A solution of N-(1(S)-ethoxycarbonyl-3-phenylpropyl)-L-alanine N-carboxylic anhydride in dichloromethane as prepared by the procedure according to the preparation example of a solution in a good solvent, 160 g (60 wt. % concentration), was added to 700 ml of normal hexane over 1 hour at 27° C. and the mixture was stirred at the same temperature for 30 minutes. The mixture was further cooled to 5° C. over 1 hour and further stirred at the same temperature for 1 hour (the weight ratio of good solvent/aliphatic hydrocarbon solvent was 0.13). The precipitated crystals of N-(1(S)-ethoxycarbonyl-3-phenylpropyl)-L-alanine N-carboxylic anhydride were collected by suction filtration using a Buchner funnel and washed with 200 ml of normal hexane. After filtration, the scale adherent to the vessel wall was separately dried and its amount was confirmed to be about 5 weight % of the total amount. Substantially no oil formation occurred. The wet crystals obtained were dried under vacuum at 25° C. for 15 hours to give 92.1 g of a dry product (recovery rate 94%, chemical purity 98%, optical purity not less than 99% e.e., mean particle diameter 20 μm).

EXAMPLE 4

A solution of N-(1(S)-ethoxycarbonyl-3-phenylpropyl)-L-alanine N-carboxylic anhydride in dichloromethane as prepared by the procedure according to the preparation example of a solution in a good solvent, 100 g (62 wt. % concentration), was added to 700 ml of normal hexane in which 1.9 g of N-(1(S)-ethoxycarbonyl-3-phenylpropyl)-L-alanine N-carboxylic anhydride crystals were suspended (the concentration of the added crystals was about 1.8 wt. %) over 15 minutes at 27° C. and the mixture was stirred at the same temperature for 30 minutes. The mixture was further cooled to 10° C. over 1 hour and stirred at the same temperature for 1 hour (the weight ratio of good solvent/aliphatic hydrocarbon solvent was 0.08). The crystals of N-(1(S)-ethoxycarbonyl-3-phenyl-propyl)-L-alanine N-carboxylic anhydride were collected by suction filtration using a Buchner funnel and washed with 80 ml of normal hexane. It was confirmed that substantially no scaling was formed at time of filtration. No oil formation occurred, either. The wet crystals obtained were dried under vacuum at 25° C. for 5 hours to give 61.4 g of a dry product (recovery rate 96%, chemical purity not less than 99%, optical purity not less than 99% e.e., mean particle diameter 40 μm).

EXAMPLE 5

A portion (5 g) of a solution (160 g) of N-(1(S)-ethoxycarbonyl-3-phenylpropyl)-L-alanine N-carboxylic anhydride in dichloromethane (62 wt. % concentration) as prepared by the procedure according to the preparation example of a solution in a good solvent was added to 700 ml of normal hexane over 15 minutes at 27° C. and the mixture was stirred at the same temperature for 30 minutes to carry out preliminary crystallization. (The weight ratio of good solvent/aliphatic hydrocarbon solvent for preliminary crystallization was 0.004 and the suspension amount of the produced slurry was 2.3 wt. %). Then, the rest of said dichloromethane solution (155 g) was added over 15 minutes at 27° C. and stirred at the same temperature for 30 minutes. The mixture was further cooled to 10° C. over 1 hour and stirred at the same temperature for 1 hour (the weight ratio of good solvent/aliphatic hydrocarbon solvent at completion of addition was 0.13). The precipitated crystals of N-(1(S)-ethoxycarbonyl-3-phenyl-propyl)-L-alanine N-carboxylic anhydride were collected by suction filtration using a Buchner funnel and washed with 130 ml of normal hexane. It was confirmed that substantially no scaling was formed at the time of filtration. Substantially no oil formation occurred, either. The wet crystals obtained were dried under vacuum at 25° C. for 15 hours to give 94.8 g of a dry product (recovery rate 95%, chemical purity not less than 99%, optical purity not less than 99% e.e., mean particle diameter 40 μm).

EXAMPLE 6

A solution of N-(1(S)-ethoxycarbonyl-3-phenylpropyl)-L-alanine N-carboxylic anhydride in dichloromethane as prepared by the procedure described in the preparation example of a solution in a good solvent, 26.4 g (62 wt. % concentration), was added to 300 ml of normal hexane over 30 minutes at 35° C. and stirred at the same temperature for 30 minutes. The mixture was further cooled to 5° C. over 3 hours and stirred at the same temperature for 1 hour (the weight ratio of good solvent/aliphatic hydrocarbon solvent was 0.05). The precipitated crystals of N-(1(S)-ethoxycarbonyl-3-phenyl-propyl)-L-alanine N-carboxylic anhydride were collected by suction filtration using a Buchner funnel and washed with 50 ml of normal hexane. After filtration, the scale adherent on the vessel wall was separately dried and its amount was confirmed to be about 2 weight % of the total amount. Substantially no oil formation occurred. The wet crystals obtained were dried under vacuum at 25° C. for 15 hours to give 15.7 g of a dry product (recovery rate 96%, optical purity not less than 99% e.e., mean particle diameter of crystals obtained was about 20 μm).

EXAMPLE 7

A solution of N-(1(S)-ethoxycarbonyl-3-phenylpropyl)-L-alanine N-carboxylic anhydride in dichloromethane as prepared by the procedure described in the preparation example of a solution in a good solvent, 131.6 g (62 wt. % concentration), was added to 152 ml of normal hexane over 30 minutes at 35° C. and the mixture was stirred at the same temperature for 30 minutes. The mixture was further cooled to 5° C. over 3 hours and stirred at the same temperature for 1 hour (the weight ratio of good solvent/aliphatic hydrocarbon solvent was 0.5). The precipitated crystals of N-(1(S)-ethoxycarbonyl-3-phenyl-propyl)-L-alanine N-carboxylic anhydride were collected by suction filtration using a Buchner funnel and washed with 150 ml of normal hexane. After filtration, the scale adherent on the vessel wall was separately dried and its amount was confirmed to be about 1 weight % of the total amount. Substantially no oil formation occurred. The wet crystals obtained were dried under vacuum at 25° C. for 15 hours to give 75.0 g of a dry product (recovery rate 92%, optical purity not less than 99% e.e., mean particle diameter of crystals obtained was about 20 μm).

EXAMPLE 8

An ethyl acetate solution containing 24.0 g of N-(1(S)-ethoxycarbonyl-3-phenylpropyl)-L-alanine N-carboxylic anhydride, 48.0 g (50 wt. % concentration), was added to 250 ml of normal hexane over 30 minutes at 35° C. and stirred at the same temperature for 30 minutes. The mixture was further cooled to 5° C. over 3 hours and stirred at the same temperature for 1 hour (the weight ratio of good solvent/aliphatic hydrocarbon solvent was 0.15). The precipitated crystals of N-(1(S)-ethoxycarbonyl-3-phenyl-propyl)-L-alanine N-carboxylic anhydride were collected by suction filtration using a Buchner funnel and washed with 60 ml of normal hexane. After filtration, the scale adherent on the vessel wall was separately dried and its amount was confirmed to be about 3 weight % of the total amount. Substantially no oil formation occurred. The wet crystals obtained were dried under vacuum at 25° C. for 15 hours to give 22.3 g of a dry product (recovery rate 93%, optical purity not less than 99% e.e., mean particle diameter of crystals obtained was about 30 μm).

EXAMPLE 9

An acetone solution containing 39.2 g of N-(1(S)-ethoxycarbonyl-3-phenylpropyl)-L-alanine N-carboxylic anhydride, 63.2 g (62 wt. % concentration), was added to 250 ml of normal hexane over 30 minutes at 30° C. and stirred at the same temperature for 30 minutes. The mixture was further cooled to 5° C. over 2.5 hours and stirred at the same temperature for 1 hour (the weight ratio of good solvent/aliphatic hydrocarbon solvent was 0.15). The precipitated crystals of N-(1(S)-ethoxycarbonyl-3-phenyl-propyl)-L-alanine N-carboxylic anhydride were collected by suction filtration using a Buchner funnel and washed with 100 ml of normal hexane. After filtration, the scale adherent on the vessel wall was separately dried and its amount was confirmed to be about 1 weight % of the total amount. Substantially no oil formation occurred. The wet crystals obtained were dried under vacuum at 25° C. for 15 hours to give 34.4 g of a dry product (recovery rate 88%, optical purity not less than 99% e.e., mean particle diameter of crystals obtained was about 40 μm).

EXAMPLE 10

A tetrahydrofuran solution containing 39.2 g of N-(1(S)-ethoxycarbonyl-3-phenylpropyl)-L-alanine N-carboxylic anhydride, 63.3 g (62 wt. % concentration), was added to 250 ml of normal hexane over 30 minutes at 35° C. and stirred at the same temperature for 30 minutes. The mixture was further cooled to 5° C. over 3 hours and stirred at the same temperature for 1 hour (the weight ratio of good solvent/aliphatic hydrocarbon solvent was 0.15). The precipitated crystals of N-(1(S)-ethoxycarbonyl-3-phenyl-propyl)-L-alanine N-carboxylic anhydride were collected by suction filtration using a Buchner funnel and washed with 100 ml of normal hexane. After filtration, the scale adherent on the vessel wall was separately dried and its amount was confirmed to be about 1 weight % of the total amount. Substantially no oil formation occurred. The wet crystals obtained were dried under vacuum at 25° C. for 15 hours to give 37.8 g of a dry product (recovery rate 96%, optical purity not less than 99% e.e., mean particle diameter of crystals obtained was about 30 μm).

EXAMPLE 11

A solution of N-(1(S)-ethoxycarbonyl-3-phenylpropyl)-L-alanine N-carboxylic anhydride in dichloromethane as prepared by the procedure according to the preparation example of a solution in a good solvent, 63.3 g (62 wt. % concentration), was added to 240 ml of isooctane over 30 minutes at 35° C. and stirred at the same temperature for 30 minutes. The mixture was further cooled to 5° C. over 3 hours and stirred at the same temperature for 1 hour (the weight ratio of good solvent/aliphatic hydrocarbon solvent was 0.15). The precipitated crystals of N-(1(S)-ethoxycarbonyl-3-phenyl-propyl)-L-alanine N-carboxylic anhydride were collected by suction filtration using a Buchner funnel and washed with 100 ml of normal hexane. After filtration, the scale adherent on the vessel wall was separately dried and its amount was confirmed to be about 1 weight % of the total amount. Substantially no oil formation occurred. The wet crystals obtained were dried under vacuum at 25° C. for 15 hours to give 38.0 g of a dry product (recovery rate 97%, optical purity not less than 99% e.e., mean particle diameter of crystals obtained was about 20 μm).

EXAMPLE 12

A solution of N-(1(S)-ethoxycarbonyl-3-phenylpropyl)-L-alanine N-carboxylic anhydride in dichloromethane as prepared by the procedure according to the preparation example of a solution in a good solvent, 63.3 g (62 wt. % concentration), was added to 235 ml of methylcyclohexane over 30 minutes at 35° C. and stirred at the same temperature for 30 minutes. The mixture was further cooled to 5° C. over 3 hours and stirred at the same temperature for 1 hour (the weight ratio of good solvent/aliphatic hydrocarbon solvent was 0.15). The precipitated crystals of N-(1(S)-ethoxycarbonyl-3-phenyl-propyl)-L-alanine N-carboxylic anhydride were collected by suction filtration using a Buchner funnel and washed with 100 ml of normal hexane. After filtration, the scale adherent on the vessel was separately dried and its amount was confirmed to be about 1 weight % of the total amount. Substantially no oil formation occurred. The wet crystals obtained were dried under vacuum at 25° C. for 15 hours to give 40.4 g of a dry product (recovery rate 95%, optical purity not less than 99% e.e., mean particle diameter of crystals obtained was about 20 μm).

EXAMPLE 13

To 253 g of a solution of N-(1(S)-ethoxycarbonyl-3-phenylpropyl)-L-alanine N-carboxylic anhydride in dichloromethane (62 wt. % concentration) as prepared by the procedure according to the preparation example of a solution in a good solvent was added 200 ml of normal hexane over 30 minutes at a temperature of 40 to 41° C. and the mixture was stirred at the same temperature for 30 minutes (the weight ratio of good solvent/aliphatic hydrocarbon solvent at this point of time was 0.71 and the suspension amount of the produced slurry was about 25 weight %) Then, 800 ml of normal hexane was added over 1 hour at a temperature of 40 to 41° C. and the mixture was stirred at the same temperature for 1 hour. The mixture was further cooled to 5° C. over 1 hour and stirred at the same temperature for 2 hours (the weight ratio of good solvent/aliphatic hydrocarbon solvent at completion of crystallization was 0.14). The precipitated crystals of N-(1(S)-ethoxycarbonyl-3-phenylpropyl)-L-alanine N-carboxylic anhydride were collected by filtration under reduced pressure using a Buchner funnel and washed with 200 ml of normal hexane (filterability was excellent). After withdrawal of the slurry from the vessel, the scaling amount was confirmed and the amount of crystals adherent on the vessel wall was found to be 2 weight % of the total amount. Substantially no oil formation occurred. The wet crystals obtained were dried under vacuum at 25° C. for 15 hours to give 145.9 g of a dry product (recovery rate 93%, chemical purity not less than 99%, optical purity not less than 99% e.e., mean particle diameter was about 400 µm). The stirring for crystallization was carried out with a stirring force corresponding to the stirring power requirement of about 0.7 to 1.3 kW/m$^3$.

EXAMPLE 14

To 63.2 g of a solution of N-(1(S)-ethoxycarbonyl-3-phenylpropyl)-L-alanine N-carboxylic anhydride in dichloromethane (62 wt. % concentration) as prepared by the procedure according to the preparation example of a solution in a good solvent was added 50 ml of normal hexane over 15 minutes at a temperature of 35° C., and 0.5 g of the above N-carboxylic anhydride was added at the same temperature. The mixture was further stirred for 30 minutes (the weight ratio of good solvent/aliphatic hydrocarbon solvent at this point of time was 0.71 and the suspension amount of the produced slurry was about 20 weight %). Then, 200 ml of normal hexane was added over 1 hour at a temperature of 35° C. and the mixture was stirred at the same temperature for 1 hour. The mixture was further cooled to 5° C. over 1 hour and stirred at the same temperature for 1 hour (the weight ratio of good solvent/aliphatic hydrocarbon solvent at completion of crystallization was 0.14). The precipitated crystals of N-(1(S)-ethoxycarbonyl-3-phenylpropyl)-L-alanine N-carboxylic anhydride were collected by suction filtration using a Buchner funnel and washed with 100 ml of normal hexane (filterability was excellent). After withdrawal of the slurry from the vessel, the scaling amount was confirmed and the amount of crystals adherent on the vessel wall was found to be 2 weight % of the total amount. Substantially no oil formation occurred. The wet crystals obtained were dried under vacuum at 25° C. for 15 hours to give 37.6 g of a dry product (recovery rate 96%, chemical purity not less than 99%, optical purity 99% e.e., mean particle diameter was about 400 µm). The stirring for crystallization was carried out with a stirring force corresponding to the stirring power requirement of about 0.5 to 1.3 kW/m$^3$.

EXAMPLE 15

To 63.3 g of a solution of N-(1(S)-ethoxycarbonyl-3-phenylpropyl)-L-alanine N-carboxylic anhydride in dichloromethane (62 wt. % concentration) as prepared by the procedure according to the preparation example of a solution in a good solvent was added 100 ml of normal hexane over 30 minutes at a temperature of 35° C. and the mixture was stirred at the same temperature for 30minutes (the weight ratio of good solvent/aliphatic hydrocarbon solvent at this point of time was 0.35). Then, 200 ml of normal hexane was added over 1 hour at a temperature of 35° C. and stirred at the same temperature for 1 hour. The mixture was further cooled to 5° C. over 1 hour and stirred at the same temperature for 1 hour (the weight ratio of good solvent/ aliphatic hydrocarbon solvent at completion of crystallization was 0.12). The precipitated crystals of N-(1(S)-ethoxycarbonyl-3-phenyl-propyl)-L-alanine N-carboxylic anhydride were collected by suction filtration using a Buchner funnel and washed with 50 ml of normal hexane (filterability was excellent). After withdrawal of the slurry from the vessel, the scaling amount was confirmed and the amount of crystals adherent on the vessel wall was found to be 1 weight % of the total amount. Substantially no oil formation occurred. The wet crystals obtained were dried under vacuum at 25° C. for 15 hours to give 37.7 g of a dry product (recovery rate 94%, chemical purity not less than 98%, optical purity not less than 99% e.e., mean particle diameter was about 380 µm). The stirring for crystallization was carried out with a stirring force corresponding to the stirring power requirement of about 0.4 to 1.3 kW/m$^3$.

EXAMPLE 16

To 63.2 g of a solution of N-(1(S)-ethoxycarbonyl-3-phenylpropyl)-L-alanine N-carboxylic anhydride in dichloromethane (62 wt. % concentration) as prepared by the procedure according to the preparation example of a solution in a good solvent was added 250 ml of normal hexane over 1.5 hours at a temperature of 45° C. and the mixture was stirred at the same temperature for 1 hour (the weight ratio of good solvent/aliphatic hydrocarbon solvent was 0.14). Then, the mixture was cooled to 5° C. over 2 hours and stirred at the same temperature for 1 hour. The precipitated crystals of N-(1(S)-ethoxycarbonyl-3-phenylpropyl)-L-alanine N-carboxylic anhydride were collected by suction filtration using a Buchner funnel and washed with 100 ml of normal hexane (filterability was excellent). After withdrawal of the slurry from the vessel, the scaling amount was confirmed and the amount of crystals adherent to the vessel wall was 3 weight % of the total amount. Substantially no oil formation occurred. The wet crystals obtained were dried under vacuum at 25° C. for 15 hours to give 37.9 g of a dry product (recovery rate 94%, chemical purity not less than 97%, optical purity not less than 99% e.e., mean particle diameter was about 300 µm). The stirring for crystallization was carried out with a stirring force corresponding to the stirring power requirement of about 0.42 to 0.8 kW/m$^3$.

EXAMPLE 17

To 131.6 g of a solution of N-(1(S)-ethoxycarbonyl-3-phenylpropyl)-L-alanine N-carboxylic anhydride in dichloromethane (62 wt. % concentration) as prepared by the procedure according to the preparation example of a solution in a good solvent was added 50 ml of normal hexane over 30 minutes at a temperature of 18 to 23° C., and the mixture was stirred at the same temperature for 30 minutes (the weight ratio of good solvent/aliphatic hydrocarbon solvent at this point of time was 1.52). Then, 102 ml of normal hexane was added over 1 hour at a temperature of 24 to 26° C. and the mixture was stirred at the same temperature for 1 hour. The mixture was further cooled to 5° C. over 2 hours and stirred at the same temperature for 1 hour (the weight ratio of good solvent/aliphatic hydrocarbon solvent at completion of crystallization was 0.5). The precipitated crystals of N-(1(S)-ethoxycarbonyl-3-phenylpropyl)-L-alanine N-carboxylic anhydride were collected by suction filtration using a Buchner funnel and washed with 200 ml of normal hexane (filterability was excellent). After withdrawal of the slurry from the vessel, the scaling amount was confirmed and the amount of crystals adherent to the vessel wall was found to be about 1 weight % of the total amount.

Substantially no oil formation occurred. The wet crystals obtained were dried under vacuum at 25° C. for 15 hours to give 75.1 g of a dry product (recovery rate 92%, chemical purity not less than 99%, optical purity not less than 99% e.e., mean particle diameter was about 200 μm) The stirring for crystallization was carried out with a stirring force corresponding to the stirring power requirement of about 0.7 to 1.3 kW/m$^3$.

EXAMPLE 18

To 26.3 g of a solution of N-(1(S)-ethoxycarbonyl-3-phenylpropyl)-L-alanine N-carboxylic anhydride in dichloromethane (62 wt. % concentration) as prepared by the procedure according to the preparation example of a solution in a good solvent was added 50 ml of normal hexane over 15 minutes at a temperature of 15 to 18° C., and the mixture was stirred at the same temperature for 30 minutes (the weight ratio of good solvent/aliphatic hydrocarbon solvent at this point of time was 0.30). Then, 250 ml of normal hexane was added over 1 hour at a temperature of 18 to 23° C. and the mixture was stirred at the same temperature for 1 hour. The mixture was further cooled to 5° C. over 2 hours and stirred at the same temperature for 1 hour (the weight ratio of good solvent/aliphatic hydrocarbon solvent at completion of crystallization was 0.05). The precipitated crystals of N-(1(S)-ethoxycarbonyl-3-phenylpropyl)-L-alanine N-carboxylic anhydride were collected by suction filtration using a Buchner funnel and washed with 60 ml of normal hexane (filterability was excellent). After withdrawal of the slurry from the vessel, the scaling amount was confirmed and the amount of crystals adherent to the vessel was about 5 weight % of the total amount. Substantially no oil formation occurred. The wet crystals obtained were dried under vacuum at 25° C. for 15 hours to give 15.2 g of a dry product (recovery rate 94%, chemical purity not less than 99%, optical purity not less than 99% e.e., mean particle diameter was about 200 μm). The stirring for crystallization was carried out with a stirring force corresponding to the stirring power requirement of about 0.7 to 1.3 kW/m$^3$.

EXAMPLE 19

To 63.2 g of a solution of N-(1(S)-ethoxycarbonyl-3-phenylpropyl)-L-alanine N-carboxylic anhydride in dichloromethane (62 wt. % concentration) as prepared by the procedure according to the preparation example of a solution in a good solvent was added 50 ml of normal hexane over 15 minutes at a temperature of 15 to 18° C., and the mixture was stirred at the same temperature for 30 minutes (the weight ratio of good solvent/aliphatic hydrocarbon solvent at this point of time was 0.73). Then, 200 ml of normal hexane was added over 1 hour at a temperature of 15 to 18° C. and the mixture was stirred at the same temperature for 1 hour. The mixture was further cooled to 5° C. over 2 hours and stirred at the same temperature for 1 hour (the weight ratio of good solvent/aliphatic hydrocarbon solvent at completion of crystallization was 0.15). The precipitated crystals of N-(1(S)-ethoxycarbonyl-3-phenylpropyl)-L-alanine N-carboxylic anhydride were collected by suction filtration using a Buchner funnel and washed with 100 ml of normal hexane (filterability was excellent). After withdrawal of the slurry from the vessel, the scaling amount was confirmed and the amount of crystals adherent to the vessel wall was about 5 weight % of the total amount. Substantially no oil formation occurred. The wet crystals obtained were dried under vacuum at 25° C. for 15 hours to give 36.7 g of a dry product (recovery rate 94%, chemical purity not less than 99%, optical purity not less than 99% e.e., mean particle diameter was about 200 μm). The stirring for crystallization was carried out with a stirring force corresponding to the stirring power requirement of about 0.7 to 1.3 kW/m$^3$.

EXAMPLE 20

To 48.0 g of an ethyl acetate solution containing 24.0 g of N-(1(S)-ethoxycarbonyl-3-phenylpropyl)-L-alanine N-carboxylic anhydride (50 wt. % concentration) was added 50 ml of normal hexane over 30 minutes at a temperature of 30° C., and the mixture was stirred at the same temperature for 30 minutes (the weight ratio of good solvent/aliphatic hydrocarbon solvent at this point of time was 0.73). Then, 200 ml of normal hexane was added over 1 hour at a temperature of 30° C. and the mixture was stirred at the same temperature for 1 hour. The mixture was further cooled to 5° C. over 3 hours and stirred at the same temperature for 1 hour (the weight ratio of good solvent/aliphatic hydrocarbon solvent at completion of crystallization was 0.15). The precipitated crystals of N-(1(S)-ethoxycarbonyl-3-phenylpropyl)-L-alanine N-carboxylic anhydride were collected by suction filtration using a Buchner funnel and washed with 100 ml of normal hexane (filterability was excellent). After withdrawal of the slurry from the vessel, the scaling amount was confirmed and the amount of crystals adherent to the vessel wall was about 2 weight % of the total amount. Substantially no oil formation occurred. The wet crystals obtained were dried under vacuum at 25° C. for 15 hours to give 23.3 g of a dry product (recovery rate 95%, chemical purity 98%, optical purity not less than 99% e.e., mean particle diameter was about 200 μm). The stirring for crystallization was carried out with a stirring force corresponding to the stirring power requirement of about 0.4 to 1.3 kW/m$^3$.

EXAMPLE 21

To 63.2 g of an acetone solution containing 39.2 g of N-(1(S)-ethoxycarbonyl-3-phenylpropyl)-L-alanine N-carboxylic anhydride (62 wt. % concentration) was added 50 ml of normal hexane over 30 minutes at a temperature of 15° C., and the mixture was stirred at the same temperature for 30 minutes (the weight ratio of good solvent/aliphatic hydrocarbon solvent at this point of time was 0.73). Then, 200 ml of normal hexane was added over 1 hour at a temperature of 15° C. and stirred at the same temperature for 1 hour. The mixture was further cooled to 5° C. over 1 hours and stirred at the same temperature for 1 hour (the weight ratio of good solvent/aliphatic hydrocarbon solvent at completion of crystallization was 0.15). The precipitated crystals of N-(1(S)-ethoxycarbonyl-3-phenyl-propyl)-L-alanine N-carboxylic anhydride were collected by suction filtration using a Buchner funnel and washed with 100 ml of normal hexane (filterability was excellent). After withdrawal of the slurry from the vessel, the scaling amount was confirmed and the amount of crystals adherent to the vessel wall was about 1 weight % of the total amount. Substantially no oil formation occurred. The wet crystals obtained were dried under vacuum at 25° C. for 15 hours to give 34.7 g of a dry product (recovery rate 88%, chemical purity 99%, optical purity not less than 99% e.e., mean particle diameter was about 200 μm). The stirring for crystallization was carried out with a stirring force corresponding to the stirring power requirement of about 0.4 to 1.3 kW/m$^3$.

EXAMPLE 22

To 63.3 g of a tetrafuran solution containing 39.3 g of N-(1(S)-ethoxycarbonyl-3-phenylpropyl)-L-alanine N-carboxylic anhydride (62 wt. % concentration) was added 50 ml of normal hexane over 30 minutes at a temperature of 30° C., and the mixture was stirred at the same temperature for 30 minutes (the weight ratio of good solvent/aliphatic hydrocarbon solvent at this point of time was 0.73). Then, 200 ml of normal hexane was added over 1 hour at a temperature of 30° C. and stirred at the same temperature for 1 hour. The mixture was further cooled to 5° C. over 2 hours and stirred at the same temperature for 1 hour (the weight ratio of good solvent/aliphatic hydrocarbon solvent at completion of crystallization was 0.15). The precipitated crystals of N-(1(S)-ethoxycarbonyl-3-phenyl-propyl)-L-alanine N-carboxylic anhydride were collected by suction filtration using a Buchner funnel and washed with 100 ml of normal hexane (filterability was excellent). After withdrawal of the slurry from the vessel, the scaling amount was confirmed and the amount of crystals adherent to the vessel wall was about 1 weight % of the total amount. Substantially no oil formation occurred. The wet crystals obtained were dried under vacuum at 25° C. for 15 hours to give 38.9 g of a dry product (recovery rate 97%, chemical purity 98%, optical purity not less than 99% e.e., mean particle diameter was about 200 µm). The stirring for crystallization was carried out with a stirring force corresponding to the stirring power requirement of about 0.4 to 1.3 kW/m$^3$.

Reference Example

A solution of N-(1(S)-ethoxycarbonyl-3-phenylpropyl)-L-alanine N-carboxylic anhydride in dichloromethane, 323.0 g (62 wt. % concentration), as prepared by the procedure described in the preparation example of a solution in a good solvent was cooled to −12° C. over 4 hours and the mixture was stirred at the same temperature for 1 hour. The precipitated crystals of N-(1(S)-ethoxycarbonyl-3-phenylpropyl)-L-alanine N-carboxylic anhydride were collected by suction filtration using a Buchner funnel (Neither scaling nor oil formation occurred). The wet crystals obtained were dried under vacuum at 25° C. for 15 hours to give 53.5 g of a dry product (recovery rate 26.7%).

For the conventional method for obtaining the compound (1), there was not known a method for obtaining crystals which have good workability on a commercial scale but according to the crystallization method of the invention, a high-purity product can be obtained as crystals with a recovery rate of not less than 90% and with large particle diameter. Moreover, the compound (1) can be recovered with its extremely high optical purity being well retained.

INDUSTRIAL APPLICABILITY

In accordance with the present invention, N-(1(S)-ethoxycarbonyl-3-phenylpropyl)-L-alanine N-carboxylic anhydride can be obtained as crystals with large mean crystal particle diameter and with good powder characteristics insuring good workability while an oil formation and scaling are inhibited by a method which can be industrially be carried out.

What is claimed is:

1. A method for crystallizing N-(1(S)-ethoxycarbonyl-3-phenylpropyl)-L-alanine N-carboxylic anhydride
comprising mixing a solution of N-(1(S)-ethoxycarbonyl-3-phenylpropyl)-L-alanine N-carboxylic anhydride in a good solvent with an aliphatic hydrocarbon solvent to crystallize said N-carboxylic anhydride,
the solution of said N-carboxylic anhydride in the good solvent being added to the aliphatic hydrocarbon solvent to thereby effect crystallization while inhibiting an oil formation and scaling of said N-carboxylic anhydride wherein the good solvent is a halogenated hydrocarbon, an ether, a nitrile, an ester, a ketone or a mixed solvent thereof.

2. The crystallization method according to claim 1 wherein a temperature at addition of the solution of N-(1(S)-ethoxycarbonyl-3-phenylpropyl)-L-alanine N-carboxylic anhydride in the good solvent to the aliphatic hydrocarbon solvent is not higher than 60° C.

3. The crystallization method according to claim 2 wherein the temperature at addition of the solution of N-(1(S)-ethoxycarbonyl-3-phenylpropyl)-L-alanine N-carboxylic anhydride in the good solvent to the aliphatic hydrocarbon solvent is −30 to 50° C.

4. The crystallization method according to claim 3 wherein the temperature at addition of the solution of N-(1(S)-ethoxycarbonyl-3-phenylpropyl)-L-alanine N-carboxylic anhydride in the good solvent to the aliphatic hydrocarbon solvent is −20 to 45° C.

5. The crystallization method according to any one of claims 1 to 4
wherein the aliphatic hydrocarbon solvent is a saturated hydrocarbon of 5 to 12 carbon atoms represented by $C_nH_{2n+2}$ or $C_nH_{2n}$, an unsaturated hydrocarbon of 5 to 12 carbon atoms represented by $C_nH_{2n}$ or $C_nH_{2n-2}$ or a mixed solvent thereof.

6. The crystallization method according to claim 5 wherein the aliphatic hydrocarbon solvent is a saturated hydrocarbon solvent of 5 to 12 carbon atoms represented by $C_nH_{2n+2}$ or $C_nH_{2n}$ or a mixed solvent thereof.

7. The crystallization method according to claim 6 wherein the aliphatic hydrocarbon solvent is pentane, 2-methylpentane, normal hexane, isohexane, normal heptane, normal octane, cyclohexane, methylcyclohexane, ethylcyclohexane, propylcyclohexane or a mixed solvent thereof.

8. The crystallization method according to claim 7 wherein the aliphatic hydrocarbon solvent is normal hexane, isohexane, normal heptane, methylcyclohexane or a mixed solvent thereof.

9. The crystallization method according to claim 1 wherein the good solvent is dichloromethane, 1,1-dichloroethane, 1,2-dichloroethane, 1,1,1-trichloroethane, 1,1,2-trichloroethane, tetrahydrofuran, 1,4-dioxane, t-butyl methyl ether, acetonitrile, ethyl acetate, methyl acetate, propyl acetate, isopropyl acetate, butyl acetate, isobutyl acetate, pentyl acetate, methyl propionate, ethyl propionate, acetone, methyl ethyl ketone or a mixed solvent thereof.

10. The crystallization method according to claim 1 wherein the good solvent is a halogenated hydrocarbon, an ether, an ester or a mixed solvent thereof.

11. The crystallization method according to claim 10 wherein the good solvent is dichloromethane, 1,1-dichloroethane, 1,2-dichloroethane, 1,1,1-trichloroethane, 1,1,2-trichloroethane, tetrahydrofuran, 1,4-dioxane, t-butyl methyl ether, ethyl acetate, methyl acetate, propyl acetate, isopropyl acetate, butyl acetate, isobutyl acetate, pentyl acetate, methyl propionate, ethyl propionate or a mixed solvent thereof.

12. The crystallization method according to claim 10 wherein the good solvent is a halogenated hydrocarbon.

13. The crystallization method according to claim 12 wherein the good solvent is dichloromethane, 1,1-dichloroethane, 1,2-dichloroethane, 1,1,1-trichloroethane, 1,1,2-trichloroethane or a mixed solvent thereof.

14. The crystallization method according to claim 13 wherein the good solvent is dichloromethane.

15. The crystallization method according to claim 1 wherein the addition of the solution of N-(1(S)-ethoxycarbonyl-3-phenylpropyl)-L-alanine N-carboxylic anhydride in the good solvent is carried out by a sequential addition.

16. The crystallization method according to claim 15 wherein the sequential addition of the solution of N-(1(S)-ethoxycarbonyl-3-phenylpropyl)-L-alanine N-carboxylic anhydride in the good solvent is carried out over not less than ¼ of an hour.

17. The crystallization method according to any one of claims 1 to 4 wherein the addition of the solution of N-(1(S)-ethoxycarbonyl-3-phenylpropyl)-L-alanine N-carboxylic anhydride in the good solvent to the aliphatic hydrocarbon solvent is carried out in a condition that a crystal of said N-carboxylic anhydride is added to said aliphatic hydrocarbon solvent in advance.

18. The crystallization method according to claim 17 wherein an amount of the crystal of N-(1(S)-ethoxycarbonyl-3-phenylpropyl)-L-alanine N-carboxylic anhydride to be added in advance is not more than 30 weight % based on the total amount of said N-carboxylic anhydride in the solution in the good solvent to be subsequently added.

19. The crystallization method according to any one of claims 1 to 4 wherein the addition of the solution of N-(1(S)-ethoxycarbonyl-3-phenylpropyl)-L-alanine N-carboxylic anhydride in the good solvent to the aliphatic hydrocarbon solvent is carried out by adding a portion of said solution in the good solvent to said aliphatic hydrocarbon solvent in advance to thereby prepare a slurry in which said N-carboxylic anhydride is precipitated, followed by adding the rest of said solution in a good solvent to said slurry.

20. The crystallization method according to claim 19 wherein an amount of the solution of N-(1(S)-ethoxycarbonyl-3-phenylpropyl)-L-alanine N-carboxylic anhydride in the good solvent to be added in advance is not more than 30 weight % based on the total amount of the solution in the good solvent to be added.

21. The crystallization method according to any one of claims 1 to 4 wherein an amount of a precipitated crystal is increased by adjusting a liquid temperature to −30 to 25° C. following completion of the addition.

22. The crystallization method according to any one of claims 1 to 4 wherein a weight ratio of the good solvent to the aliphatic hydrocarbon solvent at completion of the addition is 0.001 to 1.

23. The crystallization method according to claim 22 wherein the weight ratio of the good solvent to the aliphatic hydrocarbon solvent at completion of the addition is 0.003 to 1.

24. The crystallization method according to any one of claims 1 to 4 wherein the solution of N-(1(S)-ethoxycarbonyl-3-phenylpropyl)-L-alanine N-carboxylic anhydride in the good solvent is
an N-carboxylic anhydride forming reaction solution obtained by reacting N-(1(S)-ethoxycarbonyl-3-phenylpropyl)-L-alanine with N,N'-carbonyldiimidazole or phosgene or
a solution obtained by subjecting the reaction solution to concentration or solvent exchange.

25. The crystallization method according to claim 24 wherein an impurity or a coloring component as the by product of the N-carboxylic anhydride forming reaction is removed by using an adsorbent prior to the crystallization.

26. The crystallization method according to claim 24 wherein an N-carboxylic anhydride forming reaction solvent doubles as the good solvent for the solution of N-(1(S)-ethoxycarbonyl-3-phenylpropyl)-L-alanine N-carboxylic anhydride in the good solvent.

27. A method for crystallizing N-(1(S)-ethoxycarbonyl-3-phenylpropyl)-L-alanine N-carboxylic anhydride
comprising adding an aliphatic hydrocarbon solvent to a solution of N-(1(S)-ethoxycarbonyl-3-phenylpropyl)-L-alanine-N-carboxylic anhydride in a good solvent to crystallize said N-carboxylic anhydride,
the aliphatic hydrocarbon solvent being added sequentially over not less than ¼ of an hour and at a temperature of not higher than 60° C. to thereby inhibit an oil formation and scaling of said N-carboxylic anhydride wherein the good solvent is a halogenated hydrocarbon, an ether, a nitrile, an ester, a ketone or a mixed solvent thereof.

28. The crystallization method according to claim 27 wherein a temperature at addition of the aliphatic hydrocarbon solvent to the solution of N-(1(S)-ethoxycarbonyl-3-phenylpropyl)-L-alanine N-carboxylic anhydride in the good solvent is −30 to 50° C.

29. The crystallization method according to claim 28 wherein the temperature at addition of the aliphatic hydrocarbon solvent to the solution of N-(1(S)-ethoxycarbonyl-3-phenylpropyl)-L-alanine N-carboxylic anhydride in the good solvent is 0 to 45° C.

30. The crystallization method according to any one of claims 27 to 29 wherein the aliphatic hydrocarbon solvent is a saturated hydrocarbon of 5 to 12 carbon atoms represented by $C_nH_{2n+2}$ or $C_nH_{2n}$, an unsaturated hydrocarbon of 5 to 12 carbon atoms represented by $C_nH_{2n}$ or $C_nH_{2n-2}$, or a mixed solvent thereof.

31. The crystallization method according to claim 30 wherein the aliphatic hydrocarbon solvent is a saturated hydrocarbon of 5 to 12 carbon atoms represented by $C_nH_{2n+2}$ or $C_nH_{2n}$, or a mixed solvent thereof.

32. The crystallization method according to claim 31 wherein the aliphatic hydrocarbon solvent is pentane, 2-methylpentane, normal hexane, isohexane, normal heptane, normal octane, isooctane, normal decane, cyclopentane, cyclohexane, methylcyclohexane, ethylcyclohexane, propylcyclohexane or a mixed solvent thereof.

33. The crystallization method according to claim 32 wherein the aliphatic hydrocarbon solvent is normal hexane, isohexane, normal heptane, isooctane, methylcyclohexane or a mixed solvent thereof.

34. The crystallization method according to claim 27 wherein the good solvent is a halogenated hydrocarbon, an ether, an ester or a mixed solvent thereof.

35. The crystallization method according to claim 34 wherein the good solvent is a halogenated hydrocarbon.

36. The crystallization method according to claim 27 wherein the good solvent is dichloromethane, 1,1-dichloroethane, 1,2-dichloroethane, 1,1,1-trichloroethane, 1,1,2-trichloroethane, tetrahydrofuran, 1,4-dioxane, t-butyl methyl ether, acetonitrile, ethyl acetate, methyl acetate, propyl acetate, isopropyl acetate, butyl acetate, isobutyl acetate, pentyl acetate, methyl propionate, ethyl propionate, acetone, methyl ethyl ketone or a mixed solvent thereof.

37. The crystallization method according to claim 34 wherein the good solvent is dichloromethane, 1,1-dichloroethane, 1,2-dichloroethane, 1,1,1-trichloroethane, 1,1,2-trichloroethane, tetrahydrofuran, 1,4-dioxane, t-butyl methyl ether, ethyl acetate, methyl acetate, propyl acetate, isopropyl acetate, butyl acetate, isobutyl acetate, pentyl acetate, methyl propionate, ethyl propionate or a mixed solvent thereof.

38. The crystallization method according to claim 35 wherein the good solvent is dichloromethane, 1,1-dichloroethane, 1,2-dichloroethane, 1,1,1-trichloroethane, 1,1,2-trichloroethane or a mixed solvent thereof.

39. The crystallization method according to claim 38 wherein the good solvent is dichloromethane.

40. The crystallization method according to any one of claims 27 to 29 wherein the addition of the aliphatic hydrocarbon solvent to the solution of N-(1(S)-ethoxycarbonyl-3-phenylpropyl)-L-alanine N-carboxylic anhydride in the good solvent is carried out under stirring with a stirring force corresponding to a stirring power requirement of not less than 0.1 kW/m$^3$.

41. The crystallization method according to claim 40 wherein the addition of the aliphatic hydrocarbon solvent to the solution of N-(1(S)-ethoxycarbonyl-3-phenylpropyl)-L-alanine N-carboxylic anhydride in the good solvent is carried out under stirring with the stirring force corresponding to the stirring power requirement of not less than 0.3 kW/m$^3$.

42. The crystallization method according to any one of claims 27 to 29 wherein the addition of the aliphatic hydrocarbon solvent to the solution of N-(1(S)-ethoxycarbonyl-3-phenylpropyl)-L-alanine N-carboxylic anhydride in the good solvent is carried out by preparing a slurry of said N-carboxylic anhydride in advance and adding the aliphatic hydrocarbon solvent sequentially to said slurry.

43. The crystallization method according to claim 42 wherein a suspension amount of the slurry of said N-carboxylic anhydride to be prepared in advance is not more than 30 weight % based on the total amount of said N-carboxylic anhydride at completion of the crystallization.

44. The crystallization method according to claim 42 wherein the preparation of the slurry is carried out by sequential addition of the aliphatic hydrocarbon solvent to the solution of said N-carboxylic anhydride in the good solvent and/or by addition of a crystal of said N-carboxylic anhydride to the solution of said N-carboxylic anhydride in the good solvent.

45. The crystallization method according to claim 44 wherein the aliphatic hydrocarbon solvent is added to the solution in the good solvent in such a proportion that a weight ratio of the good solvent to the aliphatic hydrocarbon solvent is 0.1 to 10 at a preliminary crystallization.

46. The crystallization method according to any one of claims 27 to 29 wherein the weight ratio of the good solvent to the aliphatic hydrocarbon solvent is 0.001 to 1 at completion of the addition.

47. The crystallization method according to claim 46 wherein the weight ratio of the good solvent to the aliphatic hydrocarbon solvent is 0.003 to 0.8 at completion of the addition.

48. The crystallization method according to any one of claims 27 to 29 wherein an amount of a precipitated crystal is increased by adjusting a liquid temperature to −30 to 25° C. following completion of the addition.

49. The crystallization method according to any one of claims 27 to 29 wherein the solution of N-(1(S)-ethoxycarbonyl-3-phenylpropyl)-L-alanine N-carboxylic anhydride in the good solvent is an N-carboxylic anhydride forming reaction solution obtained by reacting N-(1(S)-ethoxycarbonyl-3-phenylpropyl)-L-alanine with N,N'-carbonyldiimidazole or phosgene or a solution obtained by subjecting the reaction solution to concentration or solvent exchange.

50. The crystallization method according to claim 49 wherein an impurity or a coloring component as a byproduct of the N-carboxylic anhydride forming reaction is removed by using an adsorbent prior to the crystallization.

51. The crystallization method according to claim 49 wherein an N-carboxylic anhydride forming reaction solvent doubles as the good solvent for the solution of N-(1(S)-ethoxycarbonyl-3-phenylpropyl)-L-alanine N-carboxylic anhydride in the good solvent.

* * * * *

UNITED STATES PATENT AND TRADEMARK OFFICE
CERTIFICATE OF CORRECTION

PATENT NO. : 6,784,310 B2
DATED : August 31, 2004
INVENTOR(S) : Masafumi Fukae et al.

It is certified that error appears in the above-identified patent and that said Letters Patent is hereby corrected as shown below:

Title page,
Item [12], please change "Fukae" to -- Fukae et al. --.
Item [75], Inventors, please add -- Yasuyoshi Ueda, Hyogo (JP) --.
Item [30], Foreign Application Priority Data, insert the following:
-- May 15, 2000 (JP)...2000-141717
  Oct. 30, 2000 (JP)...2000-330339
  Nov. 20, 2000 (JP)...2000-352892 --.

Signed and Sealed this

Twenty-eighth Day of June, 2005

JON W. DUDAS
*Director of the United States Patent and Trademark Office*